United States Patent
Zhang et al.

(10) Patent No.: US 10,825,554 B2
(45) Date of Patent: Nov. 3, 2020

(54) METHODS OF FEATURE EXTRACTION AND MODELING FOR CATEGORIZING HEALTHCARE BEHAVIOR BASED ON MOBILE SEARCH LOGS

(71) Applicant: Baidu USA LLC, Sunnyvale, CA (US)

(72) Inventors: Liangliang Zhang, Sunnyvale, CA (US); Jing Qian, Sunnyvale, CA (US); Yu Zhu, San Jose, CA (US); Shiyuan Fang, Sunnyvale, CA (US)

(73) Assignee: BAIDU USA LLC, Sunnyvale, CA (US)

(*) Notice: Subject to any disclaimer, the term of this patent is extended or adjusted under 35 U.S.C. 154(b) by 676 days.

(21) Appl. No.: 15/162,432

(22) Filed: May 23, 2016

(65) Prior Publication Data
US 2017/0337326 A1 Nov. 23, 2017

(51) Int. Cl.
*G16B 40/00* (2019.01)
*G16H 50/20* (2018.01)
(Continued)

(52) U.S. Cl.
CPC .......... *G16B 40/00* (2019.02); *G06F 16/951* (2019.01); *G06F 16/9535* (2019.01);
(Continued)

(58) Field of Classification Search
CPC .......... G06N 3/00; G06N 3/02; G06N 5/022; G06N 5/02; G06F 17/30758; G06F 17/30825; G06F 16/9535; G16B 40/00
(Continued)

(56) References Cited

U.S. PATENT DOCUMENTS 7,689,524 B2 * 3/2010 Ozzie ............... G06Q 10/00
706/45
9,372,898 B2 * 6/2016 Li ............... G06F 16/24578
(Continued)

FOREIGN PATENT DOCUMENTS

AU 20030217253 9/2003
CN 101053513 10/2007
(Continued)

OTHER PUBLICATIONS

Yang, Shuang-Hong et al. "Pursuing Insights about Healthcare Utilization via Geocoded Search Queries" SIGIR '13 [Published 2013] [Retrieved online May 2019] (Year: 2013).*
(Continued)

*Primary Examiner* — Vincent Gonzales
*Assistant Examiner* — Fen Christopher Tamulonis
(74) *Attorney, Agent, or Firm* — Womble Bond Dickinson (US) LLP

(57) ABSTRACT

In response to receiving a user inquiry describing one more symptoms of a medical condition, an online hospital visit prediction system can determine whether the user will visit the hospital for treatment related to the medical condition the day following the user inquiry, termed "hospital day." Query logs are stored for a large plurality of users. Using the query logs, a prediction model can be trained using predetermined features extracted from the query logs of each of a plurality of users for a predetermined period of time prior to the day the user visited the hospital. The predetermined features can be used to train the prediction model with a high accuracy to determine whether a future user will visit the hospital the day following a query about a medical condition.

27 Claims, 8 Drawing Sheets

(51) Int. Cl.
*G06N 20/00* (2019.01)
*G06N 5/02* (2006.01)
*G06F 16/951* (2019.01)
*G06F 16/9535* (2019.01)
*G16H 50/70* (2018.01)
*G16H 40/20* (2018.01)

(52) U.S. Cl.
CPC ............. *G06N 5/022* (2013.01); *G06N 20/00* (2019.01); *G16H 40/20* (2018.01); *G16H 50/20* (2018.01); *G16H 50/70* (2018.01)

(58) Field of Classification Search
USPC .......................................... 706/12, 13, 15, 21
See application file for complete search history.

(56) References Cited

U.S. PATENT DOCUMENTS

| | | | | |
|---|---|---|---|---|
| 2010/0070334 A1* | 3/2010 | Monteverde | ........... | G06Q 30/02 705/14.58 |
| 2010/0121443 A1 | 5/2010 | Michel et al. | | |
| 2011/0145183 A1 | 6/2011 | Lan et al. | | |
| 2013/0268625 A1* | 10/2013 | Agarwal | .................. | G06N 5/02 709/217 |
| 2016/0124951 A1* | 5/2016 | Barker et al. | ....... | G06F 17/3053 706/12 |
| 2017/0316085 A1* | 11/2017 | Gupta et al. | ...... | G06F 17/30401 |

FOREIGN PATENT DOCUMENTS

| | | |
|---|---|---|
| CN | 101903873 | 12/2010 |
| CN | 102971755 | 3/2013 |
| CN | 103905549 | 7/2014 |

OTHER PUBLICATIONS

White, Ryen et al. "From web search to health care utilization . . . " J Ann Med Assoc 2012 [Published 2012] [Retrieved Online May 2019 ] (Year: 2012).*

Futoma, Joseph et al. "A comparison of models for predicting early hospital readmissions" Journal of Biomedical Informatics Vo. 56 [Published 2015] [Retrieved Online May 2019] (Year: 2015).*

Wu, Zhengwei et al. "Predict user in-world activity via integration of Map Query . . . " UrbComp '15 [Published 2015] [Retrieved Online May 2019] (Year: 2015).*

White, Ryen "From Health search to healthcare: explorations of intention . . . " J Am Med Inform Assoc 2013 [Published 2013] [ Retrieved Online May 2019] (Year: 2013).*

Schoenherr, Georg et al "Interactions between Health Searchers and Search Engines" SIGIR '14 [Published 2014] [Retrieved online May 2019] (Year: 2014).*

Wang, Dakan et al. "Action Prediction and Identification From Mining Temporal User Behaviors". WSDM'11 [Published 2011] [ Retrieved Feb. 2020] <URL: https://dl.acm.org/doi/abs/10.1145/1935826.1935893> (Year: 2011).*

White, Ryen W. et al. "Web to World: Prediction Transitions . . . " AMIA 2010 Symposium [Published 2010] [Retrieved Feb. 2020] <URL: https://www.ncbi.nlm.nih.gov/pmc/articles/PMC3041420/> (Year: 2010).*

Faryar, Kiran A. "The effects of Weekday, Season, Federal Holidays . . . on Emergency Department volume . . . " Wright State University [Published 2013] [Retrieved Jun. 2020] <URL: https://corescholar.libraries.wright.edu/cgi/viewcontent.cgi?article=1094&context=mph> (Year: 2013).*

* cited by examiner

METHODS OF FEATURE EXTRACTION AND MODELING FOR CATEGORIZING HEALTHCARE BEHAVIOR BASED ON MOBILE SEARCH LOGS

FIELD OF THE INVENTION

Embodiments of the present invention relate generally to medical categorizing of healthcare behavior. More particularly, embodiments of the invention relate to automated determination of when a user will seek a treatment in relation to a medical condition.

BACKGROUND

Online-to-offline (O2O) conversion is the process of converting an online inquiry via a web search into an offline purchase in a brick-and-mortar store. O2O conversion requires detailed understanding of user behaviors. In the scenario of healthcare, modeling and accurately predicting users' probabilities of healthcare activities can help in setting up target words for pushing auxiliary content to a user in response to a search query. Auxiliary content can include medical articles related to a particular medical condition, information about doctors, hospitals, or pharmacies in a user's location, or advertising. A mobile user's search queries contain important information not only about the user's health conditions, but also the life styles, personal interests, ages, annual incomes, marital status, occupations and etc., which collectively determine the probability that a user visits a hospital in a future period. However, current prediction methods have a low effectiveness and a high computational burden.

Previous methods of determining whether, or when, a person will go to a hospital to seek a medical treatment after a search query about a medical condition are based on a single query, which contains little information on the O2O conversion rates of search queries to hospital visits. Accordingly, current methods of prediction, used for pushing auxiliary content pushed to the user based on a single query, are error prone and can decrease the users' experience in using a search engine. Machine learning based methods are used to make predictions, but feature selection for learning is a key factor that can impact the performance of a machine-learning model. Advertising and auxiliary content systems of the prior art do not select predetermine features for user healthcare behavior predictions based on mobile query history data of a large number of users.

BRIEF DESCRIPTION OF THE DRAWINGS

Embodiments of the invention are illustrated by way of example and not limitation in the figures of the accompanying drawings in which like references indicate similar elements.

DETAILED DESCRIPTION

Figure 1A:
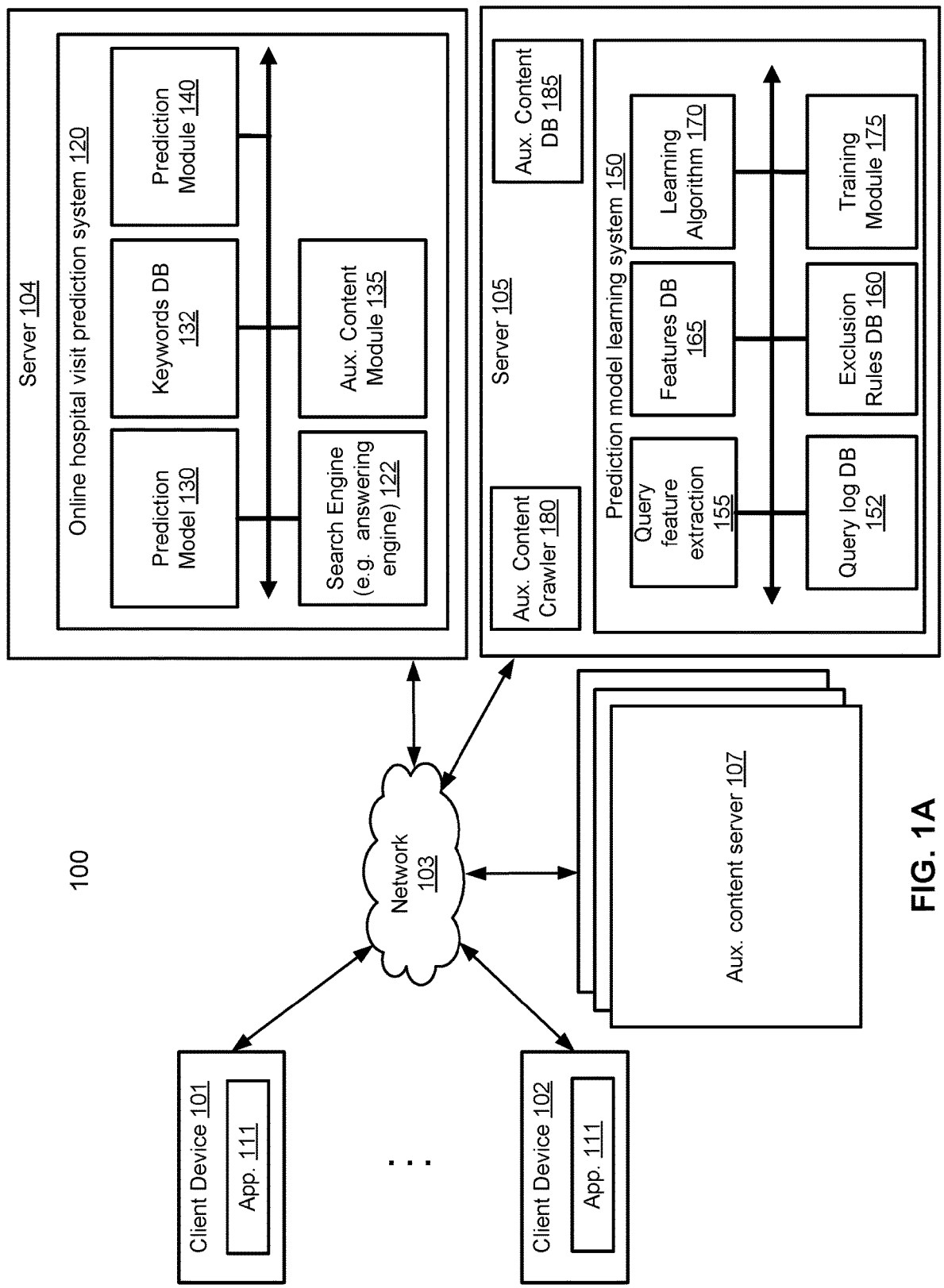
FIG. 1A is a block diagram illustrating an example of an online system for determining whether a user will go to a hospital the following day after a medical search query, according to an embodiment of the invention.

Various embodiments and aspects of the inventions will be described with reference to details discussed below, and the accompanying drawings will illustrate the various embodiments. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present inventions.

Reference in the specification to "one embodiment" or "an embodiment" means that a particular feature, structure, or characteristic described in conjunction with the embodiment can be included in at least one embodiment of the invention. The appearances of the phrase "in one embodiment" in various places in the specification do not necessarily all refer to the same embodiment.

According to some embodiments, a computer-implemented method can determine whether a user will go to the hospital for treatment of a medical condition the day after querying a system about the medical condition. The method includes receiving from an electronic device of the user, a medical query about a medical condition of the user. The method obtains, from a query log associated with the user (e.g., user interactive history), at least one previous query of the user related to the medical condition. The method then extracts one or more predetermined features from the medical query and the at least one previous medical query. At least one of the predetermined features can include a feature obtained from the medical query combined with a feature obtained from the previous medical query. The method can then determine whether the user will seek a medical treatment within a predetermined period of time (e.g., visiting a hospital the following day), and transmit a response to the medical query comprising one or more content items.

The determination can be made by applying the extracted predetermined features to a prediction model. In an embodiment, the method can transmit media content related to the medical condition, or the hospital, to the electronic device to be presented to the user. The predetermined features can include at least one of a single term obtained from the medical query combined with the hour at which the query was made, a combination of a pair of terms obtained from the medical query, or a combination of a pair of terms obtained from the medical query combined with a period of time during which the medical query was made. The pair of terms can comprise an unordered pair. In an embodiment, the at least one feature that uses both the medical query and the previous medical query can comprise a feature obtained from the medical query combined with a feature obtained from the previous medical query. The combined feature from the medical query and the feature from the previous medical query can comprise an unordered pair. The method can further include determining the day of the week that the medical query was received. Determining whether the user will visit the hospital the next day can be based at least in part on the day of the week that the medical query was received.

In another embodiment, a computer-implemented method of training a model that determines whether a user will seek a medical treatment in relation to a medical condition can include, for each of users that went to the hospital in relation to the medical condition, selecting query logs for a predetermined period of time prior to the date that the user went to the hospital in relation to the medical condition, and extracting predetermined features from the selected query logs. Predetermined features can include at least features that combine a feature from a first query log and a feature from a second query log of the selected query logs. The method can further include training the prediction model using a machine learning algorithm in response to determining that the user went to the hospital for treatment of the medical condition. The prediction model can determine whether a subsequent user will seek a medical treatment in a predetermined period of time in relation to the medical condition after the subsequent user issues a query to the system about the medical condition and updating the model based on the training.

In an embodiment, the method can further include determining the day of the week that the user sought a medical treatment and modifying the training of the prediction model based on the day of the week that the user went to the hospital. The method can also include determining that the user's visit to the hospital was not in relation to treatment of the medical condition and excluding the user's query logs and extracted features from the training of the prediction model. In an embodiment, the predetermined period can be 30 days prior to the date that the user went to the hospital for treatment for the medical condition. The machine learning algorithm can include a supervised machine learning algorithm. The machine learning algorithm can also include one of logistic regression with ridge regularizations or deep neural networks.

In an embodiment, any of the above functionality can be embodied as executable instructions stored on non-transitory computer-readable medium. In an embodiment, a system can comprise at least one hardware processor coupled to a memory comprising instructions that, when executed by the at least one hardware processor, can implement any of the above functionality.

FIG. 1A is a block diagram illustrating an example of an online system 100 for predicting whether a user will go to a hospital the following day according to an embodiment of the invention. Referring to FIG. 1A, system 100 includes, but is not limited to, one or more client devices 101-102 communicatively coupled to servers 104, and 105 over network 103. Client devices 101-102, also referred to as user devices, may be any type of client devices such as a personal computer (e.g., desktops, laptops, and tablets), a "thin" client, a personal digital assistant (PDA), a Web enabled appliance, a Smartwatch, or a mobile phone (e.g., Smartphone), etc. Network 103 may be any type of networks such as a local area network (LAN), a wide area network (WAN) such as the Internet, or a combination thereof, wired or wireless. Client devices 101 and 102 can have one or more applications 111, such as a web browser, to facilitate interaction with server 104. One or more auxiliary content servers 107 can be coupled to the network 103, and are accessible to servers 104 and 105.

According to one embodiment, user device 101 may be associated with an end user, where user device 101 may be a mobile device (e.g., tablets), a Smartphone, a Smartwatch, or a device capable of communicate with other devices over a network 103. User device 102 may be an agent device of an agent, a person or an associate associated with a particular entity or organization, where agent device 102 may also be a mobile device (e.g., tablets), a Smartphone, a Smartwatch, or a device capable of communicate with other devices over a network. For example, an agent may be associated with a content provider of a particular content item, in this example, an auxiliary content provider providing a particular auxiliary content item (e.g., sponsored content item). For the purpose of illustration, throughout the present application, communications between a user device, an agent device, and a server will be described to illustrate the techniques of tracking user and agent interactions with content items, routing data amongst a user device, an agent device, and a server, and connecting a user of the user device with an agent of the agent device. However, it will be appreciated the techniques described throughout this application can also be applied to other scenarios.

Servers 104, 105, and 107 may be any kind of server or clusters of servers, such as Web or cloud servers, application servers, backend servers, or a combination thereof. In one embodiment, server 104 can include, but is not limited to, an online hospital visit prediction system 120. In an embodiment, server 104 can also include a prediction model learning system 150. In another embodiment, prediction model learning system 150 can be on a server 105. Online hospital visit prediction system 120 can include search engine 122, prediction model 130, keywords database (DB) 132, auxiliary content module 135, and prediction module 140. Server 104 can further include an interface (not shown) to allow a client such as client devices 101-102 to access resources or services provided by server 104. The interface may include a Web interface, an application programming interface (API), and/or a command line interface (CLI).

A client user application 111 of user device 101, may send a search query to server 104 and the search query is received by search engine 122 via the interface over network 103. In response to the search query, search engine 122 can extract one or more keywords from the search query. The keywords can be used generate predetermined features that can be used by the prediction model 130 to determine whether a user will go to the hospital the day following the search query in relation to a medical condition. Keywords can be stored in keywords DB 132. Auxiliary content module 135 can use extracted features and keywords to determine auxiliary content from one or more auxiliary content servers 107 to present to the user via search engine 122 and application 111 on the client device. In an embodiment, auxiliary content can include sponsored content or promotions about hospitals, pharmacies, physicians and other care related to the medical condition that the user searched. Auxiliary content 107 can also include links to medical articles related to the medical condition, in-home care services, self-care articles, and other guidance on the medical condition. In an embodiment, auxiliary content module 135 can use keywords obtained from 132 to access auxiliary content stored auxiliary content DB 185, on server 105.

Server 105 can include a prediction model learning system 150, an auxiliary content crawler 180, and an auxiliary content database (DB) 185. Prediction model learning system 150 can alternatively be implemented on server 104. Prediction model learning system 150 can include a database of stored query logs 152 of a large number of users, and a query feature extraction model 155. Predetermined query features extracted from query logs are described in detail, below, with reference to FIG. 5. Query features extracted by query feature extraction module 155 can be stored in features database (DB) 165. Prior to storing features in features DB 165, one or more exclusion rules in exclusion rules database 160 can be applied to the extracted features to exclude the particular query log(s) that generated a set of features. For example, the query logs for a particular user can determine that the user did seek a medical treatment or go to the hospital, but the user did not stay long enough to have received the medical treatment for which the search queries were stored. This might happen if the user dropped someone off at the hospital and then left, indicating that the user did not receive treatment for the medical condition for which he searched. Alternatively, a user may have stayed too long at the hospital to have been at the hospital for a medical treatment, or went to the hospital too frequently. This could then indicate that the user may work at the hospital and did not go to the hospital for treatment for the medical condition for which the user issued one or more search queries stored in the query logs DB 152. In an embodiment, the exclusion rules DB 160 can be used to purge query logs from the query log DB 152 for which it has been determined that the user did not go to the hospital for treatment of the medical condition for which the search queries were issued.

Prediction model learning system 150 can further include a learning algorithms module 170 and a training module 175. Training module 175 can receive a learning algorithm from learning algorithm module 170, along with extracted predetermined features from features DB 165, and can train the prediction model 130 using the algorithm and features. Learning algorithms can include supervised learning algorithms. In an embodiment, learning algorithms include logistic regression with ridge regularizations and deep neural networks. The results of the training can be stored in prediction model 130. In an embodiment, prediction model 130 can be stored in online server 104. In an embodiment, prediction model 130 can be updated and stored on server 105. Online hospital visit prediction system 120 can receive the prediction model 130 from server 105 in response to a request for the prediction model 130 from online hospital visit prediction system 120. Alternatively, prediction model learning system 150 can push the updated prediction model 130 to the online hospital visit prediction system 120 when the prediction model 130 is updated.

Server 105 can further include auxiliary content crawler 180 and auxiliary content database (DB) 185. Auxiliary content crawler 180 can crawl the web, accessing auxiliary content such as on auxiliary content server(s) 107. Content obtained by auxiliary content crawler 180 can be filtered and stored on auxiliary content DB 185 so that it is readily accessible to auxiliary content module 135 on server 104. In an embodiment, storing auxiliary content in auxiliary content DB 185 can include storing a link or URL to auxiliary content and metadata related to the link or URL to the auxiliary content. In an embodiment, one or more keywords related to the auxiliary content can be stored with the auxiliary content in auxiliary content DB 185. In an embodiment, keywords related to auxiliary content can be obtained from keywords DB 132.

The user application 111 on client devices 101 and 102 may be a browser application or a mobile application if the user device is a mobile device. Search engine 122 may be a Baidu® search engine available from Baidu, Inc. or alternatively, search engine 122 may represent a Google® search engine, a Microsoft Bing™ search engine, a Yahoo® search engine, or other search engine.

A search engine 122 such as a Web search engine, is a software system that designed to search for information on the World Wide Web. The search results are generally presented in a line of results often referred to as search engine results pages. The information may be a mix of Web pages, images, and other types of files. Some search engines also mine data available in databases or open directories. Unlike web directories, which are maintained only by human editors, search engines 122 also maintain real-time information by running an algorithm on a web crawler, such as medical resource crawler 165.

Web search engines 122 work by storing information about many web pages, which they retrieve from the hypertext markup language (HTML) markup of the pages. These pages are retrieved by a Web crawler, e.g. auxiliary content web crawler 180, which is an automated Web crawler which follows every link on the site. The search engine 122 then analyzes the contents of each page to determine how it should be indexed (for example, words can be extracted from the titles, page content, headings, or special fields called meta tags). Data about web pages are stored in an index database for use in later queries. The index helps find information relating to the query as quickly as possible. In an embodiment, pages are store auxiliary content database (DB) 185.

When a user enters a query into a search engine 122 (typically by using one or more keywords), the search engine 122 examines its index and provides a listing of best-matching web pages according to its criteria, usually with a short summary containing the document's title and sometimes parts of the text. The index is built from the information stored with the data and the method by which the information is indexed. The search engine 122 looks for the words or phrases exactly as entered. Some search engines 122 provide an advanced feature called proximity search, which allows users to define the distance between keywords. There is also concept-based searching where the research involves using statistical analysis on pages containing the words or phrases you search for. As well, natural language queries allow the user to type a question in the same form one would ask it to a human.

The usefulness of a search engine 122 depends on the relevance of the result set it gives back. While there may be millions of web pages that include a particular word or phrase, some pages may be more relevant, popular, or authoritative than others. Most search engines 122 employ methods to rank the results to provide the "best" results first. How a search engine 122 decides which pages are the best matches, and what order the results should be shown in, varies widely from one engine to another.

Server 104 can correlate an identifier of a user with search activities associated with the user from interaction with search engine 122 and storage of search logs in a query log database 152. In an embodiment, an identifier of a user can be an identifier of a the electronic device that the user uses to issue search queries. In an embodiment, a user identifier can be a login, such as a login credential to utilize the search engine 122. In another embodiment, the identifier can be a randomized number, a medical record number, a medical service provider number, or other identifier. The search activity information may be captured and recorded in query log database 152 when a search was performed. In an embodiment, a query log can be associated with the identifier of the user that issued the query. The server 104 can retrieve user information of the user from query log database 152. The server 104 optionally can transmit at least some of the user information of the user from the query log database 152 to the online hospital visit prediction system 120. As a result, the user can connect and communicate with the online hospital visit prediction system 120 based on the user information of the user in the user profile 125 in a more friendly and efficient manner. Additional details of prediction model learning system 150 are described below with reference to FIG. 1C.

Figure 1B:
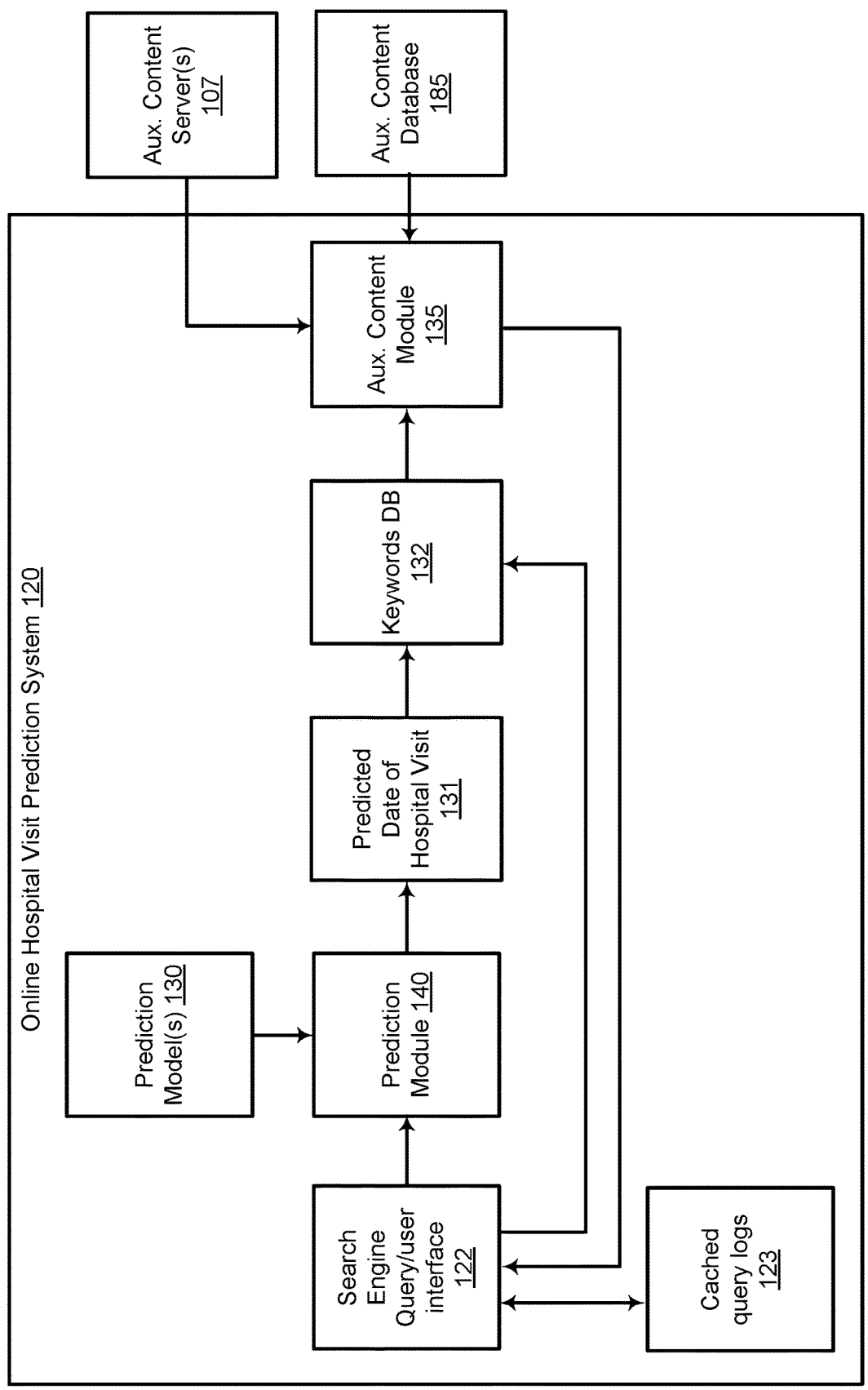
FIG. 1B is a block diagram illustrating an online system for determining whether a user will go to a hospital the following day after a medical search query, according to an embodiment of the invention.

FIG. 1B is a block diagram illustrating an online hospital visit prediction system 120 for predicting whether a user will go to a hospital the following day according to an embodiment of the invention.

A client, such as client 101, can begin using the online hospital visit prediction system 120 by issuing a medical query to query/user interface of search engine 122. In an embodiment, search engine 122 can identify a user by a hardware identification of client 101 contained within the query received from the user. In an embodiment, a user can be identified by a user login to the online hospital visit prediction system 120 or search engine 122. User queries can be cached in cached query logs 123 so that previous and subsequent ("adjacent") queries by a same user can be accessed to generate the predetermined features used by the prediction model 130, some of which utilize adjacent queries of a user. Predetermined query features are described below with reference to FIG. 5. The user's query, and one or more adjacent queries, can be parsed by the search engine 122 into one or more keywords and then generated into one or more extracted predetermined features that are passed to prediction module 140. Prediction module 140 can receive the extracted predetermined features and apply the prediction model 130 to the predetermined features to determine whether a predicted date of hospital visit 131 is the day following the user's search query. Keywords extracted from the query can be stored in keywords DB 132 and passed to auxiliary content module 135. Auxiliary content module 135 can use the stored keywords to determine auxiliary content that will be pushed to the user via search engine/web interface 122. Auxiliary content module 135 can access auxiliary content stored in auxiliary content DB 185 using keywords and/or extracted predetermined features from the search query. Alternatively, auxiliary content module 135 can use keywords and/or extracted predetermined features from the query to obtain auxiliary content from auxiliary content servers 107.

Figure 1C:
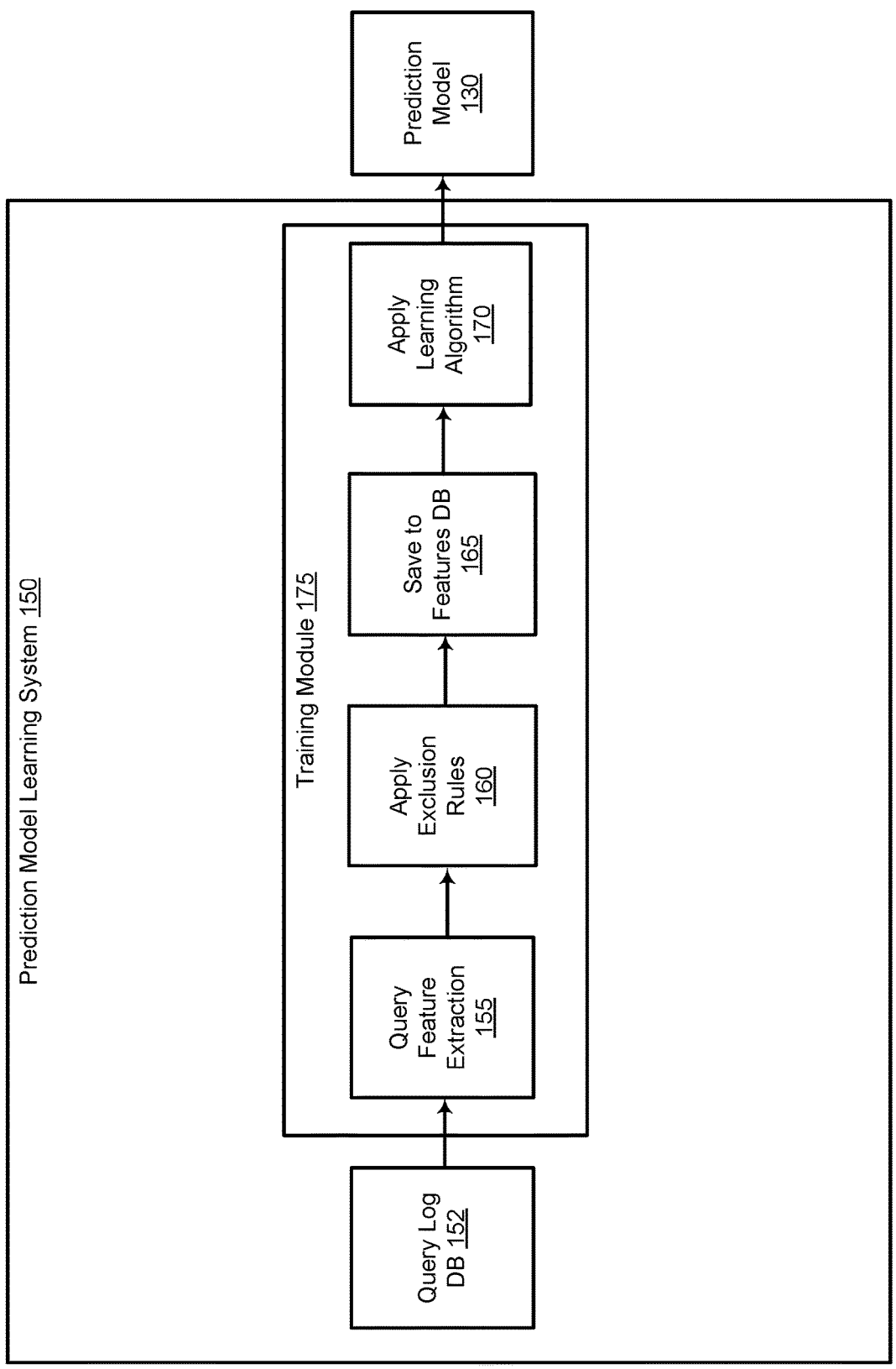
FIG. 1C is a block diagram illustrating an information and logic flow of a prediction model learning system for use in an online system that determines whether a user will go to a hospital the following day after a medical search query, according to an embodiment of the invention.

FIG. 1C is a block diagram illustrating an information and logic flow of a prediction model learning system 150 for use in an online hospital visit prediction (online HVP) system 150 according to an embodiment of the invention.

Each time a user accesses the online HVP system 120, the user's query can be stored in a query log database (query log DB) 152. Query logs in the query log DB 152 contain one or more queries of a large number of users. In an embodiment, query logs DB 152 an contain query logs of over a billion users. In an embodiment, each query can be associated with an identifier of the user such that all queries of a particular user can be extracted. Query logs can also be stamped with location data, such as GPS coordinates, one or more cell tower identifiers, a WiFi identifier, a network address, or a combination of these, to determine whether as user has gone to a hospital, and for how long the user went to the hospital. In an embodiment, each query can be stored with a date/time stamp that the query was received by search engine 122. The date/time stamp and user identifier, in combination, allow query logs for a particular user to be extracted and processed. The date/time can also be used to limit the time range of query logs extracted for a user. For example, based on location data, and time at the location, the user may have been determined to have gone to the hospital for treatment ("hospital day") of the condition for which the user issued one or more queries. If so, then query logs for the user can be extracted for a predetermined time before the hospital day. In an embodiment, the predetermined time can be 30 days prior to the hospital day.

Query features extraction module 155 can generate predetermined features extracted from the queries of each user. Predetermined query features are described below with reference to FIG. 5. The resulting query logs can be passed to a module that applies exclusion rules 160 to limit the training to only those users that have gone to the hospital for treatment of condition for which the user issued search queries. For example, exclusion rules 160 can be applied to exclude query logs for a user that may have gone to the hospital to drop someone off there (e.g. a taxi driver or family member). The user may not have been at the hospital long enough to determine that they went for treatment of the medical condition that was the subject of their search queries. Similarly, a person may go to the hospital too often, and/or stay too long at the hospital, indicating that the user works at the hospital and did not go there to seek treatment of a condition related to the user's search queries.

Extracted predetermined features for the plurality of users can be stored in features DB 165. Learning algorithm 170 can be applied to the features to generate prediction model 130. Learning algorithm 170 can be a supervised learning algorithm. The machine learning algorithm 170 can also include one of logistic regression with ridge regularizations or deep neural networks.

Figure 2:
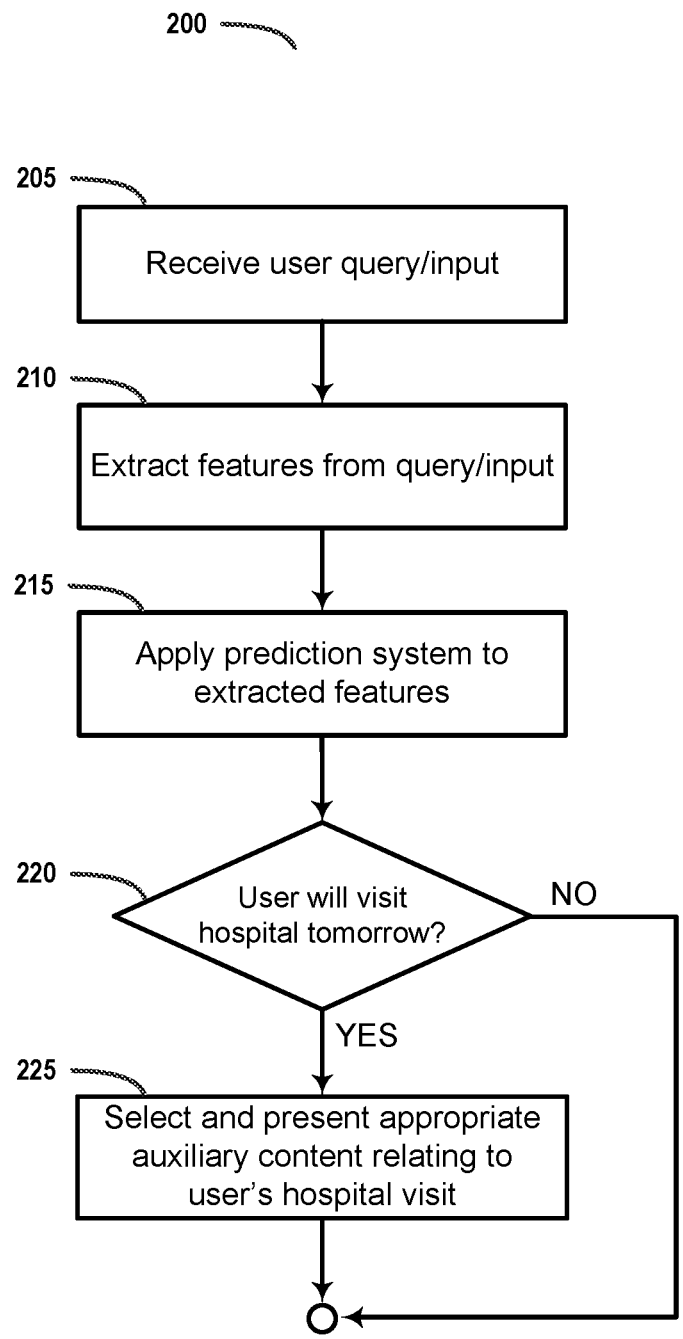
FIG. 2 is a block flow diagram of a method of determining whether a user will visit a hospital the next day after a query about a medical condition according to one embodiment of the invention.

FIG. 2 is a block flow diagram of a method 200 of determining whether a user will visit a hospital the next day after a query about a medical condition according to one embodiment of the invention. The method can be performed by processing logic which may include software, hardware, or a combination thereof.

In operation 205, search engine query/user interface 122 of online hospital visit prediction system 120 can receive a user query/input containing keywords relating to a medical condition. In operation 210, the search engine query/user interface 122 can parse the user query into one or more keywords 132 and extract predetermined features 165. In operation 215, the online hospital visit prediction system 120 can determine whether the user will visit the hospital for treatment of a medical condition the day after a query related to the medical condition. In operation 220, if the online hospital visit prediction system 120 determines that the user will seek medical treatment within a predetermined period of time, e.g., visiting the hospital the day after the query, then in operation 225, the auxiliary content module 135 within the online hospital visit prediction system 120 can select and present auxiliary content to the user via search interface 122.

Figure 3:
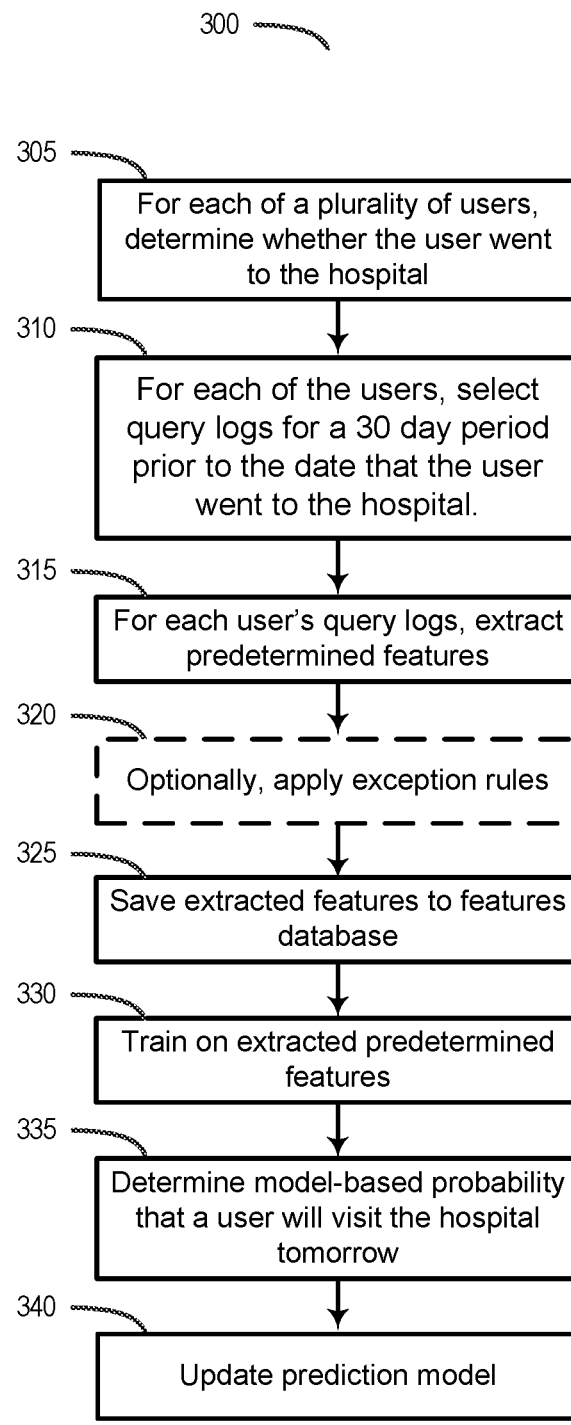
FIG. 3 is a block flow diagram of a method of training a model that determines whether a user will visit a hospital the next day after a query about a medical condition according to one embodiment of the invention.

FIG. 3 is a block flow diagram of a method 300 of training a model 130 that determines whether a user will visit a hospital the next day after a query about a medical condition according to one embodiment of the invention. The method can be performed by processing logic which may include software, hardware, or a combination thereof.

In operation 305, Query feature extraction module 155 can extract query logs from the query log database 152 for a plurality of users that have sought medical treatments, e.g., visited a hospital, for the day that the user went to the hospital ("hospital day"). Whether a user has visited a hospital, can be determined from location data stored in association with a query, correlated to known locations of medical treatment facilities such as hospitals. In operation 310, for each of the plurality of users, query logs can be extracted from query log DB 152 for a predetermined period of time prior to the hospital day. In an embodiment, the predetermined period of time can be 30 days prior to the hospital day. In operation 315, for the query logs extracted for each of the plurality of users for the predetermined period of time prior to hospital day, predetermined features can be extracted for the query logs. For the hospital day query log, a day of the week of the hospital day can be extracted as one of the predetermined features.

In operation 320, exception rules 160 can optionally be applied to exclude features of certain query logs. In an embodiment, the exception rules can be applied to purge one or more queries of a user from the query log database 152. An exception rule can be, for example, that if a user did not visit the hospital for a long enough period of time, or too long of a period of time, estimated for the medical treatment that the user went to the hospital for treatment, then the features should be excluded from training the prediction model 130 because the user was not likely at the hospital for treatment. For example, a user may have dropped someone off at the hospital and left, indicating a period time at the hospital that was too short for treatment of the medical condition. Similarly, a user may be at the hospital for too long to have been at the hospital for treatment of the medical condition, such as the user working at the hospital. In addition, a user may have been at the hospital at a time of day that a treatment, such as an elective treatment, is normally performed. In such case, a trip to the hospital, e.g. at 2:00 a.m., may indicate an emergency visit, not a visit related to a medical treatment that the user issued one or more queries about.

In operation 325, the extracted features can be saved to features database 165. In operation 330, training module 175 can select a learning algorithm 170 and apply the learning algorithm 170 to the predetermined features extracted for each of the plurality of users to generate a prediction model 130 that can determine the probability that a future user will visit a hospital the day following a search query. As a part of the training on the extracted predetermined features, the day of the week that the user visited the hospital (which is one of the predetermined features) can be used to modify the probability that a user will go the hospital the day after a search query about a medical condition. A user may be less likely (lower probability) to go to the hospital for treatment of a medical on a Monday, or mid-week, due to the interruption to the user's work week. In operation 335, a probability can be determined that a user will go to the hospital for treatment of a medical condition on the day after the user entered a search query about the medical condition. In operation 340, the prediction model 130 can be created, or updated, and stored.

Figure 4:
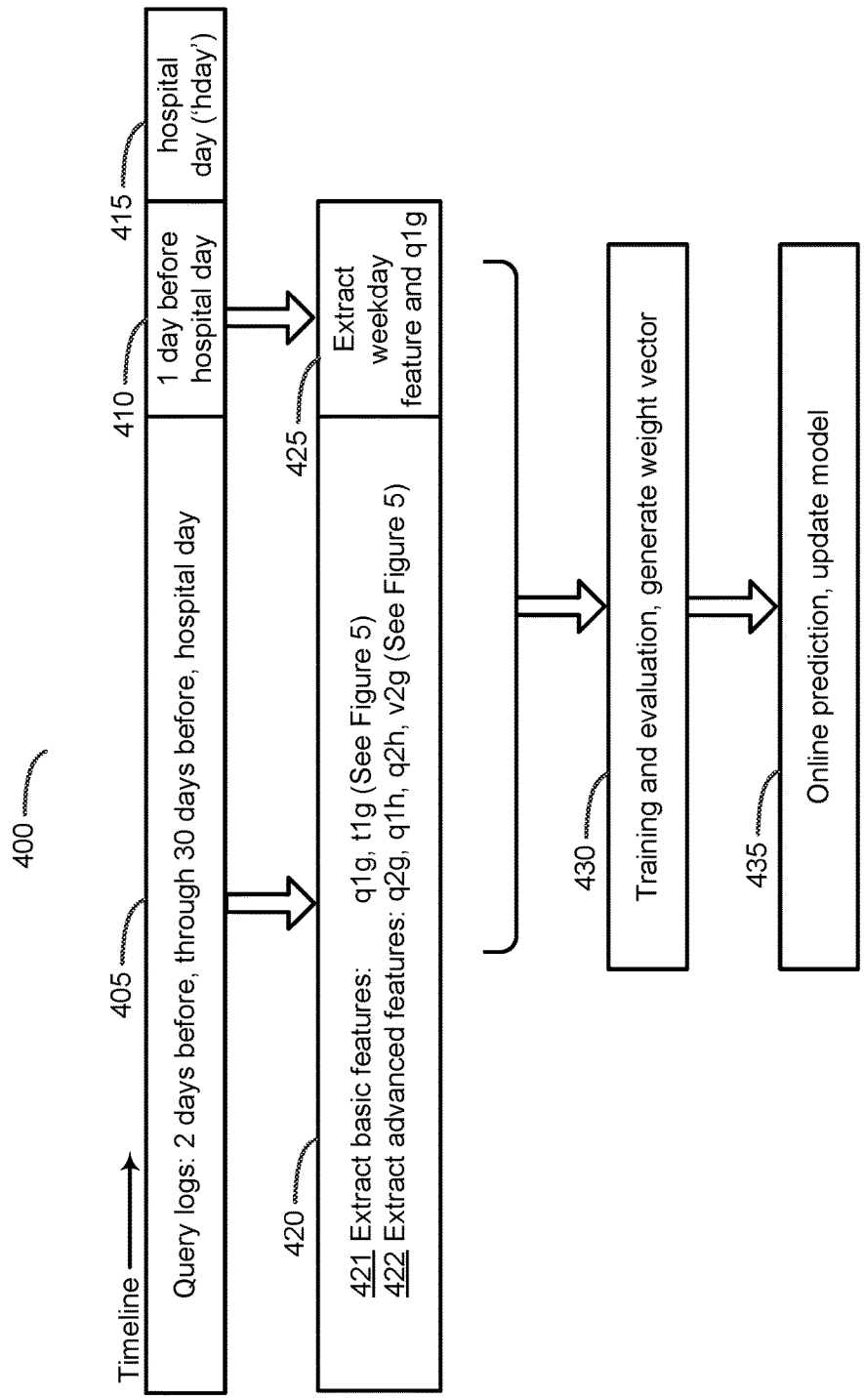
FIG. 4 is a diagram illustrating how user query logs are used by a system that determines whether a user will visit a hospital the next day after a query of the system about a medical condition according to one embodiment of the invention.

FIG. 4 is a diagram 400 illustrating how user query logs are used by a system that determines whether a user will visit a hospital the next day after a query of the system about a medical condition according to one embodiment of the invention. Elements 405, 410, and 415 illustrate a timeline for a collection of query logs for a particular user, extracted from query log database 152 or from search engine 122 cache. From location data stored in association with a query log the fact that the user visited a hospital ("hospital day" or "hday") can be determined. Using date/time information associated with the query logs for the user, the date of hospital day can be determined. Reference 410 represents the query logs 152 for the user for the day before hospital day. Reference 405 represents query logs 152 extracted for the user for the date range of 2 days before hospital day through a predetermined period of days before hospital day. In an embodiment, the predetermined period is 30 days.

Reference 420 represents extraction of predetermined basic features 421 and predetermined advanced features 422. Predetermined features are described below, with reference to FIG. 5. Basic predetermined features include a query one-gram for a plurality of terms extracted from each query of the user, and a plurality of title one-grams extracted from a title of a each query result that a user accessed. Advanced features included query two-grams, query one-gram hour, query two-gram hour, and vertical two-grams. For the query logs of the user on the day before hospital day, an additional feature termed the "weekday" feature extracts the day of the week that a user query was performed. In an embodiment, the weekday feature need only be extracted for one query on the day before hospital day, since all queries of the user on the day before hospital day will be made on the same day of the week.

In reference 430, the predetermined features extracted from query logs of the user, in a plurality of users, can be used to train a prediction model 130 and generate a weight vector for the probability that hospital day will be the day after a user issues a search query about a medical condition. In reference 435, the online prediction model 130 can be updated and stored. In an embodiment, the online prediction model 130 can be pushed to the online hospital visit prediction system 120.

Figure 5:
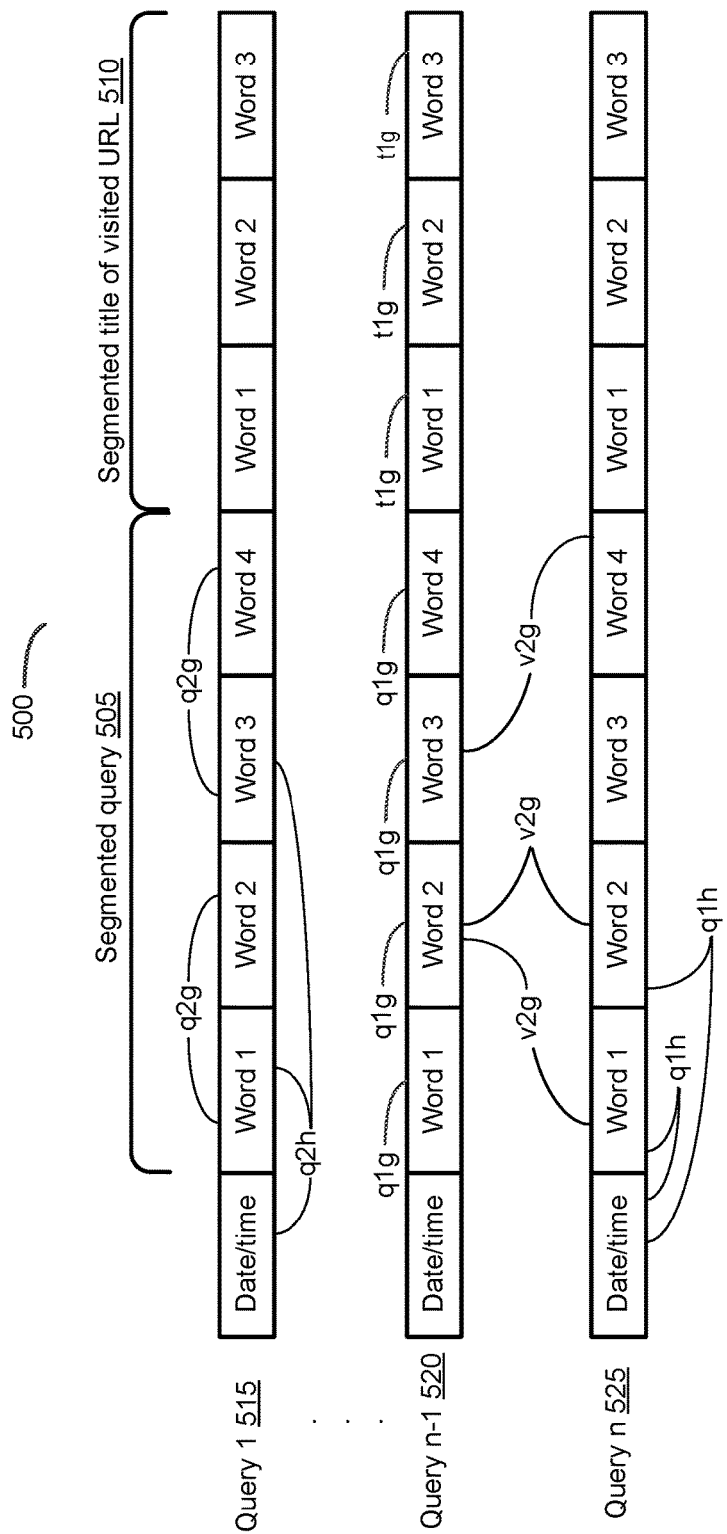
FIG. 5 is a block diagram illustrating examples of predetermined features extracted from a plurality of query logs of a user, related to a medical condition, for use by a system that determines whether the user will visit a hospital the day after a query of the system about the medical condition, according to one embodiment of the invention.

FIG. 5 is a block diagram 500 illustrating examples of predetermined features extracted from a plurality of query logs for each user in of a large number of users. Prediction model 130 can determine whether a user will visit a hospital for a medical condition the next day after the user enters a search query about the medical condition. In an embodiment, prediction model 130 is a supervised model to predict whether a user visits a hospital on a given day (called hospital day 415, or 'hday'). Internet search logs from mobile devices, and other electronic devices, are de-identified and stored in a query log database (query log DB) 152 for a large number of users. De-identified query logs from each of a large plurality of users can be identified as belonging to a person in the large plurality of users, without identifying the particular person that issued a search query. In an embodiment, query logs can be stored for over a billion users. Each query log record in query logs database 152 can contain information on the contents of the query and the time the query was made. In an embodiment, each query contains a date/time stamp when the query was received by search engine 122. Using natural language processing methods, the queries can be parsed, or segmented, into meaningful words (or word groups, if not in English). In an embodiment, the following six features are extracted from the query logs 152 of a user using a query feature extraction module 155. For the day identified as the day preceding 'hday' for a particular user's search logs, the weekday of the day preceding 'hday' is extracted as a seventh feature. The day before the day a person visits a hospital can have an influence on the user's choice to visit the hospital. For example, many users will choose not to go to the hospital on a work day. Alternatively, many users may choose to go to the hospital on Friday, so that they might recover on Saturday and Sunday, depending on the medical condition that is the reason for the hospital visit.

In the examples shown in FIG. 5, each query is segmented into four terms, Word 1 through Word 4, and each title of a result that the user selected is segmented into three terms. However, this need not be the case. The number of query terms extracted from a query or the title of a URL returned by the query and visited by the user can vary between queries and results. In an embodiment, the number of terms extracted from each query can be the same for all queries. The predetermined features extracted from the query logs are as follows:

(1) q1g: query one-gram. A query one-gram is a vector composed of single query terms extracted from a query 505. In an embodiment, the query one-gram vector has a dimension of 200K. In query 520, for example, the query can have four (4) query one-grams: Word 1, Word 2, Word 3, and Word 4, extracted from Query n−1 520. Extracted words can be filtered to exclude noise words, such as "the," "and," "a," et al.

(2) t1g: query title one-gram. A one-gram in the query title 510 is a vector composed of single query terms extracted from the title of a query result which the user selected in response to the query. In an embodiment, the query one-gram in the query title is a vector having a dimension of 100K. In query n−1 520, for example, the title 510 of the result at the selected uniform resource locator (URL) selected can be segmented into three (3) words: Word 1, Word 2, and Word 3. Extracted words can be filtered to exclude noise words, such as "the," "and," "a," et al.

(3) q2g: query two-gram. A query two-gram contains more information on the user's intentions of the query 505. A query two-gram is composed of an unordered pair of two gig's (query one-grams). Query two grams account for the fact that words searched in different orders, e.g. "cough and fever" or "fever and cough," may point to the same user search intentions. Removing the ordering information from the query two-grams obtains a good balance between accuracy and noise. In an embodiment, query two-grams are a vector having a dimension of 500K. In query 1 515, Word 1 and Word 2, and Word 3 and Word 4, are illustrations of a query two-gram. Not shown, Word 1 and Word 3, Word 1 and 4, Word 2 and Word 3, and Word 2 and Word 4 can also be query two-grams for, e.g., Query 1 515. Query two-grams can be extracted for each query 1 515 through query n 525.

(4) q1h: query one-gram with hour (time). A query one-gram with the hour of the query is a tuple containing a query one-gram (q1g) and the hour of the query (24 hours a day). In an embodiment, the query one-gram with hour vector has a dimension of 50K. As an example, Query n 525 shows the q1h tuples, Date/Time and Word 1, and Date/Time and Word 2. Not shown for Query n 525, q1h tuples also include Date/Time and Word 3, and Date/Time and Word 4. Query one-gram with hour tuples can be extracted for each query 1 515 through query n 525.

(5) q2h: query two-gram with hour (time). A query two-gram with the hour of the query is a tuple composed of a query two-gram (q2g) and the hour of the query (24 hours a day). In an embodiment, the query two-gram with hour vector has a dimension of 50K. An example query two-gram with hour is shown with reference to query 1 515 for Date/Time and the query two-gram Word 1 and Word 3. A query two-gram with hour can be formed using Date/Time and any query two-gram, as described above for (3) q2g. Query two-grams with hour tuples can be extracted for each of query 1 515 through query n 525.

(6) v2g: a vertical query two-gram is obtained by combining a query one-gram from each of two successive (adjacent) queries. In an embodiment, the vertical query two-grams are ordered pairs, whose order is determined by the order of the successive (adjacent) queries. In an embodiment, vertical query two-grams are unordered pairs of query-one grams from each of two successive (adjacent) queries. Vertical query two-grams provide more accurate information on the intention of the user because many users perform additional searches based their initial search results to get more detailed or comparative results. Vertical query two-grams can be formed using any query one-gram from a first query and any query one-gram from a subsequent, adjacent query. In an embodiment, the vertical query two-gram vector has a dimension of 500K.

(7) weekday feature: a 7 dimensional vector that represent which day (Monday~Sunday) is the date we are predicting. Users' healthcare activities are strongly dependent on whether it is weekends or weekdays. In an embodiment, the weekday feature is extracted from query log(s) of the user the day before the hospital day and is used to determine hospital day. In an embodiment, the weekday feature can be extracted from query logs of the user on hospital day.

In an embodiment, positive and negative training samples can be selected from the extracted features (1)-(7). The training of the model can be done by both logistic regression with ridge regularizations, and by deep neural networks. Testing has shown an area under the curve of 89% with accuracy greater than 85% using these seven predetermined features, suggesting the predetermined features are very effective to predicting users healthcare activities.

Figure 6:
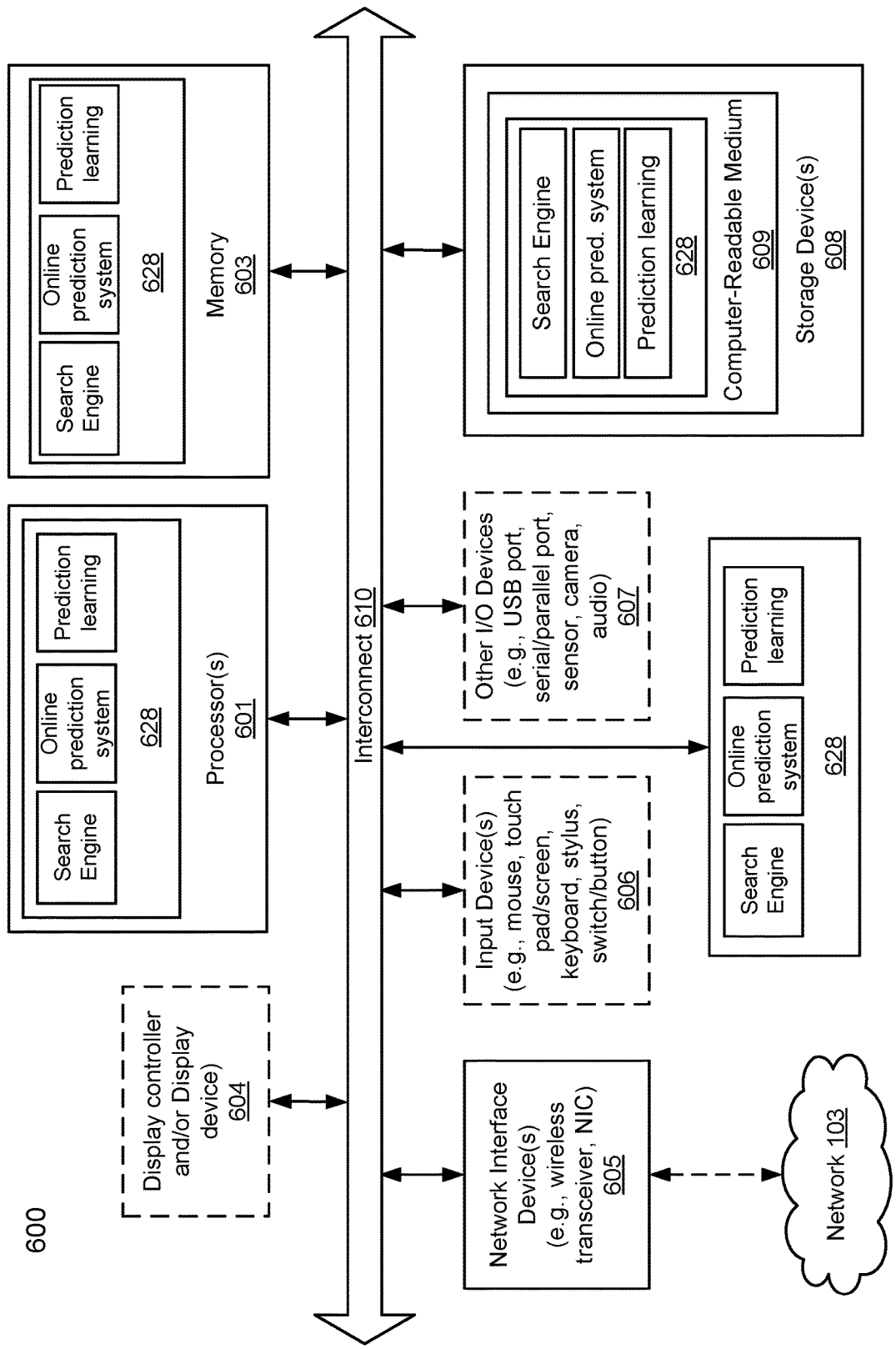
FIG. 6 is a block diagram illustrating a data processing system according to one embodiment.

FIG. 6 is a block diagram illustrating an example of a data processing system 600 which may be used with one embodiment of the invention. For example, system 600 may represent any of data processing systems described above performing any of the processes or methods described above, such as, for example, a client device 101 or 102, a server 102, or server 104 described above.

System 600 can include many different components. These components can be implemented as integrated circuits (ICs), portions thereof, discrete electronic devices, or other modules adapted to a circuit board such as a motherboard or add-in card of the computer system, or as components otherwise incorporated within a chassis of the computer system.

Note also that system 600 is intended to show a high level view of many components of the computer system. However, it is to be understood that additional components may be present in certain implementations and furthermore, different arrangement of the components shown may occur in other implementations. System 600 may represent a desktop, a laptop, a tablet, a server, a mobile phone, a media player, a personal digital assistant (PDA), a Smartwatch, a personal communicator, a gaming device, a network router or hub, a wireless access point (AP) or repeater, a set-top box, or a combination thereof. Further, while only a single machine or system is illustrated, the term "machine" or "system" shall also be taken to include any collection of machines or systems that individually or jointly execute a set (or multiple sets) of instructions to perform any one or more of the methodologies discussed herein.

In one embodiment, system 600 includes processor 601, memory 603, and devices 605-608 via a bus or an interconnect 610. Processor 601 may represent a single processor or multiple processors with a single processor core or multiple processor cores included therein. Processor 601 may represent one or more general-purpose processors such as a microprocessor, a central processing unit (CPU), or the like. More particularly, processor 601 may be a complex instruction set computing (CISC) microprocessor, reduced instruction set computing (RISC) microprocessor, very long instruction word (VLIW) microprocessor, or processor implementing other instruction sets, or processors implementing a combination of instruction sets. Processor 601 may also be one or more special-purpose processors such as an application specific integrated circuit (ASIC), a cellular or baseband processor, a field programmable gate array (FPGA), a digital signal processor (DSP), a network processor, a graphics processor, a network processor, a communications processor, a cryptographic processor, a co-processor, an embedded processor, or any other type of logic capable of processing instructions.

Processor 601, which may be a low power multi-core processor socket such as an ultra-low voltage processor, may act as a main processing unit and central hub for communication with the various components of the system. Such processor can be implemented as a system on chip (SoC). Processor 601 is configured to execute instructions for performing the operations and steps discussed herein. System 600 may further include a graphics interface that communicates with optional graphics subsystem 604, which may include a display controller, a graphics processor, and/or a display device.

Processor 601 may communicate with memory 603, which in one embodiment can be implemented via multiple memory devices to provide for a given amount of system memory. Memory 603 may include one or more volatile storage (or memory) devices such as random access memory (RAM), dynamic RAM (DRAM), synchronous DRAM (SDRAM), static RAM (SRAM), or other types of storage devices. Memory 603 may store information including sequences of instructions that are executed by processor 601, or any other device. For example, executable code and/or data of a variety of operating systems, device drivers, firmware (e.g., input output basic system or BIOS), and/or applications can be loaded in memory 603 and executed by processor 601. An operating system can be any kind of operating systems, such as, for example, Windows® operating system from Microsoft®, Mac OS®/iOS® from Apple, Android® from Google®, Linux®, Unix®, or other real-time or embedded operating systems such as VxWorks.

System 600 may further include IO devices such as devices 605-608, including network interface device(s) 605, optional input device(s) 606, and other optional IO device(s) 607. Network interface device 605 may include a wireless transceiver and/or a network interface card (NIC). The wireless transceiver may be a WiFi transceiver, an infrared transceiver, a Bluetooth transceiver, a WiMax transceiver, a wireless cellular telephony transceiver, a satellite transceiver (e.g., a global positioning system (GPS) transceiver), or other radio frequency (RF) transceivers, or a combination thereof. The NIC may be an Ethernet card.

Input device(s) 606 may include a mouse, a touch pad, a touch sensitive screen (which may be integrated with display device 604), a pointer device such as a stylus, and/or a keyboard (e.g., physical keyboard or a virtual keyboard displayed as part of a touch sensitive screen). For example, input device 606 may include a touch screen controller coupled to a touch screen. The touch screen and touch screen controller can, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with the touch screen.

IO devices 607 may include an audio device. An audio device may include a speaker and/or a microphone to facilitate voice-enabled functions, such as voice recognition, voice replication, digital recording, and/or telephony functions. Other IO devices 607 may further include universal serial bus (USB) port(s), parallel port(s), serial port(s), a printer, a network interface, a bus bridge (e.g., a PCI-PCI bridge), sensor(s) (e.g., a motion sensor such as an accelerometer, gyroscope, a magnetometer, a light sensor, compass, a proximity sensor, etc.), or a combination thereof. Devices 607 may further include an imaging processing subsystem (e.g., a camera), which may include an optical sensor, such as a charged coupled device (CCD) or a complementary metal-oxide semiconductor (CMOS) optical sensor, utilized to facilitate camera functions, such as recording photographs and video clips. Certain sensors may be coupled to interconnect 610 via a sensor hub (not shown), while other devices such as a keyboard or thermal sensor may be controlled by an embedded controller (not shown), dependent upon the specific configuration or design of system 600.

To provide for persistent storage of information such as data, applications, one or more operating systems and so forth, a mass storage (not shown) may also couple to processor 601. In various embodiments, to enable a thinner and lighter system design as well as to improve system responsiveness, this mass storage may be implemented via a solid state device (SSD). However in other embodiments, the mass storage may primarily be implemented using a hard disk drive (HDD) with a smaller amount of SSD storage to act as a SSD cache to enable non-volatile storage of context state and other such information during power down events so that a fast power up can occur on re-initiation of system activities. Also a flash device may be coupled to processor 601, e.g., via a serial peripheral interface (SPI). This flash device may provide for non-volatile storage of system software, including a basic input/output software (BIOS) as well as other firmware of the system.

Storage device 608 may include computer-accessible storage medium 609 (also known as a machine-readable storage medium or a computer-readable medium) on which is stored one or more sets of instructions or software (e.g., module, unit, and/or logic 628) embodying any one or more of the methodologies or functions described herein.

Module/unit/logic 628 may represent any of the components described above, such as, for example, a search engine, an online prediction system, or a prediction learning system as described above. Module/unit/logic 628 may also reside, completely or at least partially, within memory 603 and/or within processor 601 during execution thereof by data processing system 600, memory 603 and processor 601 also constituting machine-accessible storage media. Module/unit/logic 628 may further be transmitted or received over a network via network interface device 605.

Computer-readable storage medium 609 may also be used to store the some software functionalities described above persistently. While computer-readable storage medium 609 is shown in an exemplary embodiment to be a single medium, the term "computer-readable storage medium" should be taken to include a single medium or multiple media (e.g., a centralized or distributed database, and/or associated caches and servers) that store the one or more sets of instructions. The terms "computer-readable storage medium" shall also be taken to include any medium that is capable of storing or encoding a set of instructions for execution by the machine and that cause the machine to perform any one or more of the methodologies of the present invention. The term "computer-readable storage medium" shall accordingly be taken to include, but not be limited to, solid-state memories, and optical and magnetic media, or any other non-transitory machine-readable medium.

Module/unit/logic 628, components and other features described herein can be implemented as discrete hardware components or integrated in the functionality of hardware components such as ASICS, FPGAs, DSPs or similar devices. In addition, module/unit/logic 628 can be implemented as firmware or functional circuitry within hardware devices. Further, module/unit/logic 628 can be implemented in any combination hardware devices and software components.

Note that while system 600 is illustrated with various components of a data processing system, it is not intended to represent any particular architecture or manner of interconnecting the components; as such details are not germane to embodiments of the present invention. It will also be appreciated that network computers, handheld computers, mobile phones, servers, and/or other data processing systems which have fewer components or perhaps more components may also be used with embodiments of the invention.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the preceding figures may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

In the foregoing specification, embodiments of the invention have been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A computer-implemented method for predicting whether a user is likely to go to a medical treatment facility to obtain medical treatment for a medical condition of the user the day after a medical query by the user about the medical condition, the method comprising:

receiving, at a server from an electronic device of the user over a network, the medical query about the medical condition of the user;

in response to the medical query, obtaining by a processor of the server a previous medical query of the user related to the medical condition from a query log containing a plurality of queries associated with the user, wherein the previous medical query is adjacent to the medical query, wherein each query in the plurality of queries in the query log of the user includes a date/time stamp and a location of the electronic device at the time the query was issued, wherein the date/time stamp comprises both a date and a time;

extracting by the processor a plurality of predetermined features from the medical query and the previous medical query of the user, wherein the predetermined features include a location of the electronic device when the medical query was issued, a query two-gram obtained by combining a first term obtained from the medical query combined with a second term obtained from the previous medical query, a query one-gram-hour obtained from a term of the medical query and the time from the date/time stamp of the medical query, and a weekday feature obtained from the date/time stamp of the medical query indicating a day of the week of the medical query;

determining whether the user is likely to go to the medical treatment facility to obtain medical treatment for the medical condition the day after the medical query by the user about the medical condition, wherein the determining is based on the extracted predetermined features from the medical query and the previous medical query, and a predictive model trained using query logs from a plurality of users who have obtained medical treatment for the medical condition, and the determining is based at least in part on the query two-gram, query one-gram-hour, weekday feature, and the predictive model; and transmitting a response to the electronic device over the network, the response including one or more content items that are identified based on a likelihood that the user will seek medical treatment the day following the medical query.

2. The method of claim 1, further comprising:
transmitting media content related to the medical condition to the electronic device to be presented to the user.

3. The method of claim 1, wherein the query log further includes a log entry of an interaction by the user with at least one query result returned by the medical query, and wherein the predetermined features further include:
a combination of a first pair of terms obtained from the medical query, and
a combination of a second pair of terms obtained from a title of the query result that the user interacted with.

4. The method of claim 3, wherein the first and second pair of terms are each an unordered pair.

5. The method of claim 1, wherein at least one of the plurality of predetermined features comprises two terms of the medical query and the time from the date/time stamp of the medical query.

6. The method of claim 1, wherein the location of the electronic device is determined by one or more of: GPS coordinates, one or more cell tower identifiers, a WiFi identifier, a network address, or a combination of these, and determining the location of the electronic device further comprises determining whether the location of the electronic device correlates to a known location of the medical treatment facility.

7. The method of claim 1, wherein the predictive model returns a lower likelihood that the user will seek medical treatment the day after the medical query in response to determining that the day after the medical query is a Monday and a higher likelihood that the user will seek medical treatment after the medical query in response to determining that the day after the medical query is a Friday.

8. A non-transitory computer-medium having stored thereon executable instructions that, when executed by at least one hardware processor, perform operations for predicting whether a user is likely to go to a medical treatment facility to obtain medical treatment for a medical condition of the user the day after a medical query by the user about the medical condition, the operations comprising:
receiving, at a server from an electronic device of the user over a network, the medical query about the medical condition of the user;
in response to the medical query, obtaining by a processor of the server a previous medical query of the user related to the medical condition from a query log containing a plurality of queries associated with the user, wherein the previous medical query is adjacent to the medical query, wherein each query in the plurality of queries in the query log of the user includes a date/time stamp and a location of the electronic device at the time the query was issued, wherein the date/time stamp comprises both a date and a time;
extracting by the processor a plurality of predetermined features from the medical query and the previous medical query of the user, wherein the predetermined features include location of the electronic device when the a medical query was issued, a query two-gram obtained by combining a first term obtained from the medical query and a second term obtained from the previous medical query, a query one-gram-hour obtained from a term of the medical query and the time from the date/time stamp of the medical query, and a weekday feature obtained from the date/time stamp of the medical query indicating a day of the week of the medical query;
determining whether the user is likely to go to the medical treatment facility to obtain medical treatment for the medical condition the day after the medical query by the user about the medical condition, wherein the determining is based on the extracted predetermined features from the medical query and the previous query, and a predictive model trained using query logs from a plurality of users who have obtained medical treatment for the medical condition, and the determining is based at least in part on the query two-gram, query one-gram-hour, the weekday feature, and the predictive model;
and transmitting a response to the electronic device over the network, the response including one or more content items that are identified based on a likelihood that the user will seek medical treatment the day following the medical query.

9. The medium of claim 8, further comprising:
transmitting media content related to the medical condition to the electronic device to be presented to the user.

10. The medium of claim 8, wherein the query log further includes a log entry of an interaction by the user with at least one query result returned by the medical query, and wherein the predetermined features further include:
a combination of a first pair of terms obtained from the medical query, and
a combination of a second pair of terms obtained from a title of the query result that the user interacted with.

11. The method of claim 10, wherein the first and second pair of terms are each an unordered pair.

12. The medium of claim 8, wherein at least one of the plurality of predetermined features comprises two terms of the medical query and the time from the date/time stamp of the medical query.

13. The method of claim 8, wherein the location of the electronic device is determined by one or more of: GPS coordinates, one or more cell tower identifiers, a WiFi identifier, a network address, or a combination of these, and determining the location of the electronic device further comprises determining whether the location of the electronic device correlates to a known location of the medical treatment facility.

14. The medium of claim 8, wherein the predictive model returns a lower likelihood that the user will seek medical treatment the day after the medical query in response to determining that the day after the medical query is a Monday and a higher likelihood that the user will seek medical treatment after the medical query in response to determining that the day after the medical query is a Friday.

15. A system comprising at least one hardware processor coupled to a memory, the memory having stored thereon executable instructions that, when executed by the at least one hardware processor, perform operations for predicting whether a user is likely to go to a medical treatment facility to obtain medical treatment for a medical condition of the user the day after a medical query by the user about the medical condition, the operations comprising:
receiving, at a server from an electronic device of the user over a network, the medical query about the medical condition of the user;
in response to the medical query, obtaining by a processor of the server a previous medical query of the user related to the medical condition from a query log containing a plurality of queries associated with the user, wherein the previous medical query is adjacent to the medical query, wherein each query in the plurality of queries in the query log of the user includes a date/time stamp and a location of the electronic device at the time the query was issued, wherein the date/time stamp comprises both a date and a time;

extracting by the processor a plurality of predetermined features from the medical query and the previous medical query of the user, wherein the predetermined features include a location of the electronic device when the medical query was issued, a query two-gram obtained by combining a first term obtained from the medical query combined with a second term obtained from the previous medical query, a query one-gram-hour obtained from a term of the medical query and the time from the date/time stamp of the medical query, and a weekday feature obtained from the date/time stamp of the medical query indicating a day of the week of the medical query;

determining whether the user is likely to go to the medical treatment facility to obtain medical treatment for the medical condition the day after the medical query by the user about the medical condition, wherein the determining is based on the extracted predetermined features from the medical query and the previous medical query, and a predictive model trained using query logs from a plurality of users who have obtained medical treatment for the medical condition, and the determining is based at least in part on the query two-gram, query one-gram-hour, weekday feature, and the predictive model; and transmitting a response to the electronic device over the network, the response including one or more content items that are identified based on a likelihood that the user will seek medical treatment the day following the medical query.

16. The system of claim 15, further comprising: transmitting media content related to the medical condition, or the medical treatment facility, to the electronic device to be presented to the user.

17. The method of claim 15, wherein the query log further includes a log entry of an interaction by the user with at least one query result returned by the medical Query and wherein the predetermined features further include:
a combination of a first pair of terms obtained from the medical query, and
a combination of a second pair of terms obtained from a title of the query result that the user interacted with.

18. The method of claim 17, wherein the first and second pair of terms are each an unordered pair.

19. The system of claim 15, wherein at least one of the plurality of predetermined features comprises two terms of the medical query and the time from the date/time stamp of the medical query.

20. The method of claim 15, wherein the location of the electronic device is determined by one or more of: GPS coordinates, one or more cell tower identifiers, a WiFi identifier, a network address, or a combination of these, and determining the location of the electronic device further comprises determining whether the location of the electronic device correlates to a known location of the medical treatment facility.

21. The system of claim 15, further comprising:
determining a day of a week that the medical query was received, wherein determining whether the user will seek medical treatment the day after the medical query is based at least in part on the day of the week that the medical query was received.

22. A computer-implemented method of training a model that predicts whether a user is likely to go to a hospital to obtain treatment for a medical condition of the user the day after a medical query by the user about the medical condition, the method comprising:
for each of a plurality of users that obtained medical treatment for the medical condition:
selecting query logs of the user for a predetermined number of days prior to a date that the user obtained the medical treatment in relation to the medical condition, wherein each query within the query logs contains a date/time stamp, wherein the date/time stamp comprises a date and a time;
identifying the day the user went to the medical treatment facility for medical treatment for the medical condition, using location information associated with each query in the selected query logs of the user;
selecting a medical query that was issued the day before the day that the user went to the medical treatment facility for medical treatment for the medical condition, and a previous medical query, adjacent to the medical query, wherein the medical query and the previous medical query were both in relation to the medical condition;
extracting a plurality of predetermined features from the medical query and the previous medical query, wherein the predetermined features comprises a location of the electronic device when the medical query was issued, a query two-gram obtained by combining a first term obtained from the medical query of the user and a second term obtained from the previous medical query, the predetermined features further include a one-gram-hour obtained from a term of the medical query and the time from the date/time stamp of the medical query, and the predetermined features further include a day of the week that the user obtained medical treatment for the medical condition, wherein each query includes a location of an electronic device that issued the query;
training the model using a machine learning algorithm and the predetermined features from the query logs, wherein the model determines when a subsequent user is likely to obtain medical treatment for the medical condition the day after the subsequent user issues a query about the medical condition; and
updating the model based on the training.

23. The method of claim 22, further comprising:
determining a day of a week that the user sought the medical treatment; and
modifying the training of the model based on the day of the week that the user sought the medical treatment.

24. The method of claim 22, wherein the location of the location of the electronic device is determined by one or more of: GPS coordinates, one or more cell tower identifiers, a WiFi network identifier, a network address, or a combination of these, and the method further comprising:
determining whether the location of the electronic device correlates to a known location of the medical treatment facility; and
in response to determining that the user's visit to the medical treatment facility was not in relation to a treatment of the medical condition excluding the user's query logs and extracted features from the training of the model.

25. The method of claim 22, wherein the predetermined period is 30 days prior to the date that the user went to the medical treatment facility for treatment for the medical condition.

26. The method of claim 22, wherein the machine learning algorithm comprises a supervised machine learning algorithm.

27. The method of claim 22, wherein the machine learning algorithm comprises one of:
- logistic regression with ridge regularization; or
- a deep neural network.

\* \* \* \* \*